US00PP14039P39

(12) United States Plant Patent
Meilland

(10) Patent No.: US PP14,039 P3
(45) Date of Patent: Jul. 29, 2003

(54) HYBRID TEA ROSE PLANT NAMED 'MEIKAROUZ'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 37 days.

(21) Appl. No.: 09/933,175

(22) Filed: Aug. 21, 2001

(65) Prior Publication Data

US 2002/0144318 P1 Oct. 3, 2002

(30) Foreign Application Priority Data

Mar. 30, 2001 (FR) ..... 17655

(51) Int. Cl.[7] ..... A01H 5/00
(52) U.S. Cl. ..... Plt./140
(58) Field of Search ..... Plt./139, 140

*Primary Examiner*—Howard J. Locker
(74) *Attorney, Agent, or Firm*—Burns, Doane, Swecker & Mathis, L.L.P.

(57) ABSTRACT

A new and distinct variety of Hybrid Tea rose plant is provided which abundantly forms attractive fragrant very double blossoms that are velvety dark red in coloration. The plant exhibits a semi-upright growth habit, dense medium green semi-glossy foliage, and good vigor. A strong fragrance also is displayed. The new variety is particularly well suited for growing as attractive ornamentation in the landscape such as in parks and gardens.

1 Drawing Sheet

Figures 2, 3, 4, 5, 6, 7, 8, 9, 10, 11, 12, 13, 14, 15, 16:
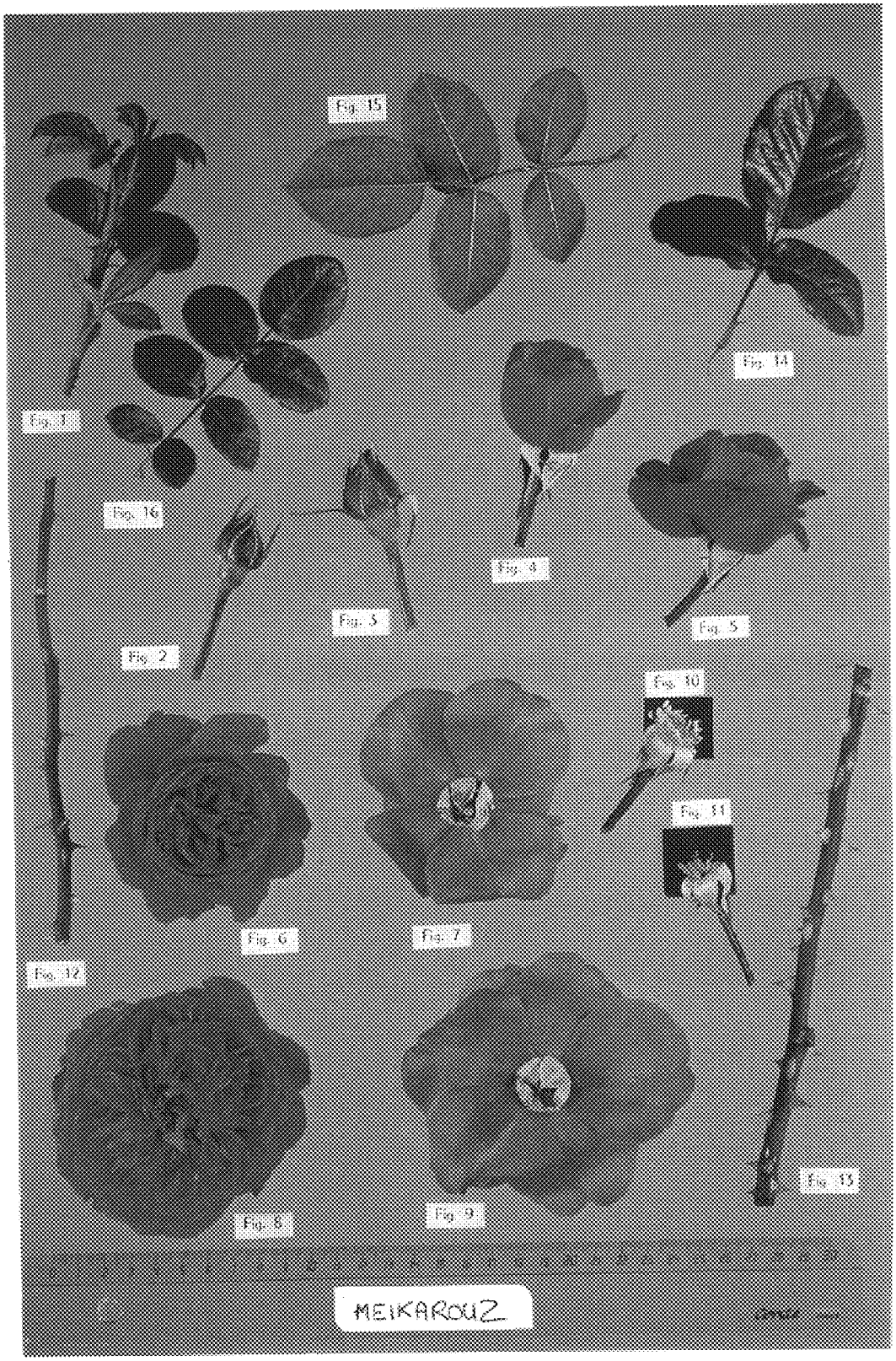

BOTANICAL/COMMERCIAL CLASSIFICATION: *Rosa hybrida*/Hybrid Tea Rose Plant.
VARIETAL DENOMINATION: cv. 'Meikarouz'.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) is the 'Meihirvin' variety (non-patented in the United States). The male parent (i.e., the pollen parent) was the product of the pollination of the 'Meinuzeten' variety (U.S. Plant Pat. No. 4,224) and the 'Meicapula' variety (non-patented in the United States). The parentage of the new variety can be summarized as follows:

'Meihirvin'×('Meinuzeten'×'Meicapula').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) exhibits a semi-upright growth habit,
(b) abundantly forms attractive fragrant very double blossoms that are velvety dark red in coloration,
(c) forms dense medium green semi-glossy foliage,
(d) exhibits good vigor, and
(e) is particularly well suited for growing as attractive ornamentation in the landscape.

The new variety well meets the needs of the horticultural industry and can be grown to advantage in parks and gardens.

The new variety of the present invention can be readily distinguished from its ancestors. More specifically the red flowers of the 'Meihirvin' variety are quartered when fully open. The flowers of the 'Meinuezten' variety are red-orange in coloration on the obverse, golden yellow on the reverse, and commonly display a substantially lesser petal number of approximately 33 on average. The flowers of the 'Meicapula' variety are medium pink in coloration and also possess a lesser number of petals that commonly averages approximately 35.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meikarouz' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa laxa* understock and growing in outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud at the beginning of the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during June while budded on *Rosa laxa* understock and growing outdoors at Le Cannet des Maures, Var, France. The coloration in more common terms precedes reference to the chart in some instances. Such terminology is to be accorded its ordinary dictionary significance.

Class: Hybrid Tea.

Plant:

*Height.*—Approximately 90 to 100 cm at the end of the growing season.

*Width.*—Approximately 60 to 80 cm at the end of the growing season.

*Habit.*—Semi-upright.

Branches:

*Color.*—Young stems: near Green Group 137A. Adult wood: near Yellow-Green Group 146A.

*Thorns.*—Size: large (as illustrated). Quantity: moderately numerous (as illustrated). Color: near Greyed-Yellow Group 162A at the base and near Greyed-Orange Group 164A at the tip. Configuration: slightly concave at the under surface.

Leaves:

*Stipules.*—Adnate, pectinate, and narrow.

*Petioles.*—Near Green Group 137A with some reddish-brown anthocyanin coloration on the upper surface and near Yellow-Green Group 146B on the under surface.

*Leaflets.*—Number: 3, 5 (most often), and 7. Shape: elliptic-ovate, bear a generally symmetrical obtuse base and generally symmetrical broad point (as illustrated). Serration: regular (as illustrated). Texture: consistent and rather firm. General appearance: very dense, medium green, and semi-glossy foliage. Color (young foliage): Upper surface: near Green Group 137A with some anthocyanin coloration of Greyed-Red Group 178A. Under surface: near Yellow-Green Group 146A with some anthocyanin coloration of Greyed-Red Group 178A. Color (adult foliage): Upper surface: near Green Group 137A. Under surface: near Yellow-Green Group 146A.

Inflorescence:

*Number of flowers.*—Usually one flower per stem.

*Peduncle.*—Near Yellow-Green Group 146B with strong anthocyanin coloration approaching Greyed-Orange Group 175D, medium in size, and the length is approximately 4.5 to 5 cm on average.

*Stem length.*—Flowering stems commonly measure approximately 60 to 70 cm on average.

*Sepals.*—Upper surface: tomentose, glandular, commonly lacking extensions, and near Greyed-Green Group 194B in coloration. Under surface: near Yellow-Green Group 146B with slight anthocyanin coloration that approaches Greyed-Orange Group 166A. Configuration: elongated.

*Buds.*—Shape: ovoid. Length: approximately 2 cm on average. Color: Upper surface: velvety red, near Red Group 45A. Under surface: Blood Red, near Red Group 45D.

*Flower.*—Shape: very double and cup-shaped. Diameter: approximately 11 to 12 cm on average. Color (when opening begins): Upper surface: velvety red, near Red Group 45A. Under surface: Geranium Lake, near Red Group 47D. Color (when blooming): Upper surface: velvety red, near Red Group 45A. Under surface: Geranium Lake, near Red Group 47D. Color (at end of blooming): Upper surface: velvety red, near Red Group 45A. Under surface: Geranium Lake, near Red Group 47D. Fragrance: strong. Lasting quality: very long on the plant (e.g., approximately 12 days on average). The specific longevity of flowers when cut and placed in a vase has not been evaluated since the variety is primarily intended for providing ornamentation outdoors in the landscape. Petal shape: displays a pointed wedge-shaped base and a rounded slightly reflexed tip. The external petals are slightly cordate in configuration. Petal number: approximately 144 to 153 on average. Stamen number: approximately 46 on average. Anthers: near Yellow Group 11A in coloration. Filaments: near Yellow Group 11D in coloration. Pollen: present in a moderate quantity and near Yellow-Orange Group 14D in coloration. Pistil number: approximately 97 on average. Stigmas: near Red Group 47C in coloration. Styles: near Yellow Group 11D in coloration. Petal drop: the petals commonly detach cleanly. Receptacle: near Yellow-Green Group 146B in coloration, and funnel-shaped in longitudinal section.

Development:

*Vegetation.*—Very vigorous and strong.

*Blooming.*—Very abundant.

*Resistance to diseases.*—Generally good with respect to Powdery Mildew, but displays some susceptibility to Black Spot.

*Aptitude to bear fruit.*—None.

I claim:

1. A new and distinct variety of Hybrid Tea rose plant characterized by the following combination of characteristics:

(a) exhibits a semi-upright growth habit, (b) abundantly forms attractive fragrant very double blossoms that are velvety dark red in coloration, (c) forms dense medium green semi-glossy foliage, (d) exhibits good vigor, and (e) is particularly well suited for growing as attractive ornamentation in the landscape;

substantially as herein shown and described.

* * * * *

MEIKAROUZ